United States Patent
Yates et al.

(10) Patent No.: US 11,407,653 B2
(45) Date of Patent: Aug. 9, 2022

(54) METHOD, SYSTEM AND APPARATUS FOR MONITORING AND CONTROLLING WATER QUALITY AND FLOW

(71) Applicant: INSTANTIA LABS INC., St. Catharines (CA)

(72) Inventors: Colin Yates, Saint Catharines (CA); Andre Boysen, Saint Catharines (CA); Sam Mula, Huntsville (CA)

(73) Assignee: INSTANTIA LABS, INC., Ontario (CA)

( * ) Notice: Subject to any disclaimer, the term of this patent is extended or adjusted under 35 U.S.C. 154(b) by 160 days.

(21) Appl. No.: 16/304,512

(22) PCT Filed: May 26, 2017

(86) PCT No.: PCT/IB2017/053130
§ 371 (c)(1),
(2) Date: Nov. 26, 2018

(87) PCT Pub. No.: WO2017/203491
PCT Pub. Date: Nov. 30, 2017

(65) Prior Publication Data
US 2019/0135657 A1    May 9, 2019

Related U.S. Application Data

(60) Provisional application No. 62/342,043, filed on May 26, 2016.

(51) Int. Cl.
*C02F 1/00* (2006.01)
*E03B 7/07* (2006.01)
(Continued)

(52) U.S. Cl.
CPC .............. *C02F 1/008* (2013.01); *E03B 7/071* (2013.01); *E03B 7/075* (2013.01); *E03B 7/078* (2013.01); *G01M 3/28* (2013.01); *G01M 3/2807* (2013.01); *G01N 33/18* (2013.01); *G01N 33/182* (2013.01); *G01N 33/1813* (2013.01); *G01N 33/1826* (2013.01); *C02F 2209/02* (2013.01);
(Continued)

(58) Field of Classification Search
CPC ............. C02F 1/008; E03B 7/07; E03B 7/071
See application file for complete search history.

(56) References Cited

U.S. PATENT DOCUMENTS 5,971,011 A    10/1999    Price
7,110,920 B2    9/2006    McCarter et al.
(Continued)

FOREIGN PATENT DOCUMENTS

CN    203259202 U    10/2013
WO    WO-2012/156966 A1    11/2012

*Primary Examiner* — Walter L Lindsay, Jr.
*Assistant Examiner* — Andrew V Do
(74) *Attorney, Agent, or Firm* — Harness, Dickey & Pierce, PLC

(57) ABSTRACT

A water quality and flow monitoring and control apparatus, method and system installed at an end user location and being capable of monitoring one or more of the following water quality parameters: microorganisms (including *E. coli*), mineral or other ion concentration, pH, temperature, and turbidity. The system also has a water meter that detects the flow of water and has a valve to shut the flow of water off upon detecting a fault condition such as a leak.

7 Claims, 7 Drawing Sheets

(51) Int. Cl.
  *G01M 3/28* (2006.01)
  *G01N 33/18* (2006.01)
  *G01F 15/063* (2022.01)

(52) U.S. Cl.
  CPC ....... *C02F 2209/06* (2013.01); *C02F 2209/11* (2013.01); *C02F 2209/29* (2013.01); *C02F 2209/36* (2013.01); *C02F 2209/40* (2013.01); *C02F 2307/14* (2013.01); *G01F 15/063* (2013.01); *G01N 2033/184* (2013.01)

(56) References Cited

U.S. PATENT DOCUMENTS

| | | |
|---|---|---|
| 7,360,413 B2 | 4/2008 | Jeffries et al. |
| 7,412,876 B2 | 8/2008 | Kates |
| 7,669,461 B2 | 3/2010 | Kates |
| 8,279,080 B2 | 10/2012 | Pitchford et al. |
| 8,479,598 B2 | 7/2013 | Vincent |
| 8,486,342 B2 | 7/2013 | Hooper et al. |
| 8,583,386 B2 | 11/2013 | Armon et al. |
| 9,749,792 B2 * | 8/2017 | Klicpera ................. E03B 7/071 |
| 2002/0070107 A1 * | 6/2002 | Usinowicz .............. C02F 9/005 |
| | | 204/228.3 |
| 2009/0158819 A1 | 6/2009 | Vincent |
| 2011/0178644 A1 * | 7/2011 | Picton .................... E03B 7/071 |
| | | 700/282 |

* cited by examiner

METHOD, SYSTEM AND APPARATUS FOR MONITORING AND CONTROLLING WATER QUALITY AND FLOW

CROSS-REFERENCE TO RELATED APPLICATIONS

This application is a National Stage of International Patent Application No. PCT/IB2017/053130, filed May 26, 2017, which claims priority to U.S. Provisional Patent Application No. 62/342,043 filed May 26, 2016. The entire disclosures of each of the above applications are incorporated herein by reference.

TECHNICAL FIELD

The present invention relates to methods, systems and apparatus for monitoring and controlling water quality and flow. More particularly, an embodiment of the present invention relates to methods, systems and apparatus that may be installed and/or used at an end user location and being capable of monitoring one or more of the following water related parameters: micro-organisms (such as bacteria, including *E. coli*), mineral or other ion content and/or concentration (such as chlorine, nitrates, sodium, etc.), pH, temperature, and turbidity. The embodiments of the present invention may also include water monitoring apparatus (such as water meters) that measure the flow of water and water control mechanisms (such as water valves) to shut the flow of water off upon detecting a fault or alert condition (such as a leak or change in pressure).

BACKGROUND

Various water leak detection systems incorporating water shut-off valves are generally known. The following patents, for example, describe certain types of these devices: (a) U.S. Pat. No. 5,971,011 to Price, Oct. 26, 1999; (b) U.S. Pat. No. 7,360,413 to Jeffries et al., Apr. 22, 2008; (c) U.S. Pat. No. 7,412,876 to Kates, Aug. 19, 2008; (d) U.S. Pat. No. 7,669,461 to Kates, Mar. 2, 2010; (e) U.S. Pat. No. 8,279,080 to Pitchford et al., Oct. 2, 2012; (f) U.S. Pat. No. 8,479,598 to Vincent, Jul. 9, 2013; (g) U.S. Pat. No. 8,583,386 to Armon et al., Nov. 12, 2013; (h) U.S. Pat. No. 8,489,342 to Drugger et al., Jul. 16, 2013; and (i) Chinese Patent No. 203259202, Oct. 30, 2013.

However, the devices described in these patents differ from the present invention, and fail to achieve the advantages of the present invention.

SUMMARY

The present invention may be directed to an apparatus, method and/or system that may be installed at an end user location, such as, for example, a residence or commercial building. The apparatus or device of the present invention may be installed "in-pipe", allowing water to directly flow past (e.g be in contact with) one or more sensors located within the device. The apparatus, method and/or system of the present invention may be capable of monitoring one or more of the following water parameters, such as: (a) pathogens, such as, microorganisms, such as bacteria (including, but not limited to, *E. coli*, Heterotrophic Plate Count, total coliforms), enteric viruses and parasites (including, but not limited to *Legionella, Cryptosporidium, Giardia lamblia*); (b) mineral ion or other ion concentrations (including, but not limited to chlorine (e.g. chlorite, chloramines, chlorine dioxide, etc.), calcium, sodium. lead, copper, and heavy metals, such as, but not limited to arsenic species, and cadmium (c) pH, (d) nitrogen (nitrate, nitrite, ammonia/ammonium), (e) temperature, (f) turbidity, (g) flow (e.g. volume per unit time) and (h) pressure.

The apparatus, method and/or system of the present invention may also include water measuring devices (including, but not limited to flow meters) that detect the volume of water passing through the pipe over a given time. The apparatus or device of the present invention may have also water control mechanisms (such as water valves, etc.) so as to allow a user to shut off the flow of water, for example, at any desired time, such as, for example, upon detecting a "alert condition" or a "fault condition" such as a leak (i.e. low pressure detection) or adverse water quality.

It may be an aspect of the present invention to provide an apparatus, method and/or system having a variety of water parameter testing features that may be adapted for use at an end user location such as, for example, in a private residence or commercial building. In particular, it may be an aspect of the present invention to be able to test water parameters in real time and provide immediate or real time feedback to provide security over water drinking quality, water flow and other characteristics. It may be also an aspect to provide a water meter in the same system that detects the flow of water and detects leaks in order to lower the risk of flooding due to leaks in the plumbing of the user locations remote from the location of the apparatus of the present invention.

Still yet another important aspect of the invention may be to provide analytics concerning the flow and quality of water to residential users, utility companies, and/or commercial entities.

In one embodiment, the invention comprises an apparatus, method and/or system that can be installed at an end user location, the system having: (a) a water meter to detect a flow of water through the device and determine volume of water passing through; (b) a valve capable of blocking the flow of water upon detecting an alert condition; and (c) a device capable of monitoring one or more of the following water quality parameters including, but not limited to: (i) the presence of pathogens, such as bacteria (including, but not limited to, *E. coli*), Heterotrophic Plate Count, total coliforms, enteric viruses and parasites (including, but not limited to *Legionella, Cryptosporidium, Giardia lamblia*); (ii) the presence of mineral ions or other ion concentrations (including but not limited to chlorine (chlorite, chloramines, chlorine dioxide), calcium, sodium, lead, copper and heavy metals, including but not limited to arsenic species, and cadmium; (iii) pH; (iv) nitrogen (nitrate, nitrite, ammonia/ammonium) concentration; (v) temperature; (vi) turbidity; (vii) flow (e.g. volume per unit time); and (viii) pressure.

In yet another preferred embodiment, specific algorithms are used determine the nature of each water consuming or taking events (e.g. tap being turned on, dishwasher etc.), including adverse events or alert conditions, such as, for example, leaks. In the event of an adverse water event an alert may be sent to a location manager or owner who has the ability to take action either through direct onsite action or remotely (e.g. via a web dashboard). The water monitoring system of the present invention, employing apparatus 2, can detect whether the adverse event or alert condition (in the case of a leak, for example) may be internal to the user location (downstream from outlet pipe 13) or external to the user location (upstream from outlet pipe 10). In a preferred embodiment at least two control mechanisms 18 can be placed before and after the water quality and monitoring device 2 containing the sensors 14. Using a pressure sensor, the system can detect pressure prior or after the device using analytics in a corresponding server connected (via WIFI or other means) to the device. In a preferred embodiment, this can be done by the system performing verification tests. For example, if on control mechanism is shut off prior to the device/pressure sensor and pressure is observed to continue to decrease it can be determined that a leak is likely occurring after control mechanism. If, no pressure loss was observed then the leak may be occurring prior to the device/pressure and control mechanism.

A further embodiment of the present invention provides an apparatus for in-pipe measuring of water quality and quantity at a user location, the apparatus comprising: (a) a housing having a water inlet port and a water outlet port having a water flow thorough the device during operation; (b) a processor disposed with the housing; (c) a water quantity measuring device in the housing and disposed in the water flow for measuring a water quantity parameter of the water within the water flow and transmitting the water quantity parameter to the processor; (d) a water quality measuring device in the housing and disposed in the water flow for measuring a water quality parameter of the water within the water flow and transmitting said water quality parameter to the processor; and (e) a water control mechanism in the housing for controlling the water flow for controlling the flow of water.

Yet further embodiment is provided wherein the water quality parameter is selected from the group consisting of microorganism concentration, ion concentration (e.g. mineral or other ions), pH, temperature, and turbidity.

Yet further embodiment is provided wherein the user location is a residence or commercial building.

Yet further embodiment is provided wherein the water quantity parameter is selected from the group consisting of water flow and water pressure.

Yet further embodiment is provided the water control mechanism is a water valve.

Yet further embodiment is provided wherein the water control mechanism allows a user to shut off the flow of water manually, automatically or upon a fault condition.

Yet further embodiment is provided the processor wirelessly transmits the water quality and quantity parameters and events (e.g. leaks) to a remote server.

Yet further embodiment is provided the water control mechanism controls the flow of water out of the water inlet outlet.

Yet further embodiment is provided the processor wirelessly transmits the water quality and quantity parameters to a remote server in real time.

Yet further embodiment is provided further comprising a second water control mechanism for controlling the water flow through the water inlet and through the device.

Yet further embodiment is provided wherein the water quality and quantity data and/or parameters are provided to residential users, utility companies, and/or commercial entities.

Yet further embodiment is provided wherein the microorganism is selected from the group consisting of bacteria, viruses and parasites.

Yet further embodiment is provided wherein the bacteria are selected from the group consisting of *E. coli*, Heterotrophic Plate Count, and total coliforms, Yet further embodiment is provided wherein the viruses are enteric viruses.

Yet further embodiment is provided wherein the parasites are selected from the group consisting of *Legionella, Cryptosporidium*, and *Giardia lamblia*.

Yet further embodiment is provided wherein the ion is selected from the group consisting of chlorine, chlorite, chloramines, chlorine dioxide, calcium, sodium, lead, copper, heavy metals, nitrogen, nitrate, nitrite, and ammonia/ammonium.

Yet further embodiment provides a method for controlling the flow of water at a user location by in-pipe measuring of water quality and quantity, the method comprising: (a) providing an in-pipe water monitoring device at a location proximate to the water inlet of the user location, the in-pipe water monitoring device comprising; (i) a housing having a water inlet port and a water outlet port having a water flow thorough the device during operation; (ii) a processor disposed with the housing; (iii) a water quantity measuring device in the housing and disposed in the water flow for measuring a water quantity parameter of the water within the water flow and transmitting the water quantity parameter to the processor; (iv) a water quality measuring device in the housing and disposed in the water flow for measuring a water quality parameter of the water within the water flow and transmitting said water quality parameter to the processor; and (v) a water control mechanism in the housing for controlling the water flow for controlling the flow of water; and (b) stopping the flow of water into the user location based on the water quantity parameter or the water quality parameter.

Yet another preferred embodiment of the present invention is a method to detect whether a suspected leak is either before the device or after the device by manipulating the control valve. A further preferred embodiment is directed to a method for detecting whether an adverse event is internal to a user location or external to the user location, the method comprising: (a) installing a device as noted above having a first and second control mechanism, the first control mechanism downstream from an inlet pipe and the second control mechanism upstream from an outlet pipe 10; (b) detecting the water pressure loss within the device; (c) shutting off the first control mechanism and determining of there is a pressure loss detected within the device; wherein if a pressure loss is detected, the adverse event has occurred internal to a user location and if a pressure loss is not detected the adverse event has occurred external to the user location.

Further and other aspects of the invention may become apparent to those skilled in the relevant art from the following detailed description of the embodiments thereof.

BRIEF DESCRIPTION OF DRAWINGS

Reference may now be had to the following detailed description taken together with the accompanying drawings in which.

DETAILED DESCRIPTION

The description that follows, and the embodiments described therein, is provided by way of illustration of an example, or examples, of particular embodiments of the principles and aspects of the present invention. These examples are provided for the purposes of explanation, and not of limitation, of those principles and of the invention.

It should also be appreciated that the present invention can be implemented in numerous ways, including as a process, method, an apparatus, a system, a device or the like. In this specification, these implementations, or any other form that the invention may take, may be referred to as apparatus, systems and processes/methods. In general, the order of the steps of the disclosed processes may be altered within the scope of the invention.

As used herein, an "alert condition" or "fault condition" will be understood by a person skilled in the relevant art to mean a condition, typically an adverse event, in which the water flow should be discontinued. Such alert conditions may arise from various scenarios, including, but not limited to, detection of a loss of pressure by the pressure sensor, unusually or long periods of water use as detected through a flow meter (e.g. based on average user data) and/or pressure sensor and/or poor water quality as detected through the turbidity sensor. It will also be understood to encompass any condition in which a user may wish to stop the flow of water for any other reason.

Figure 1:
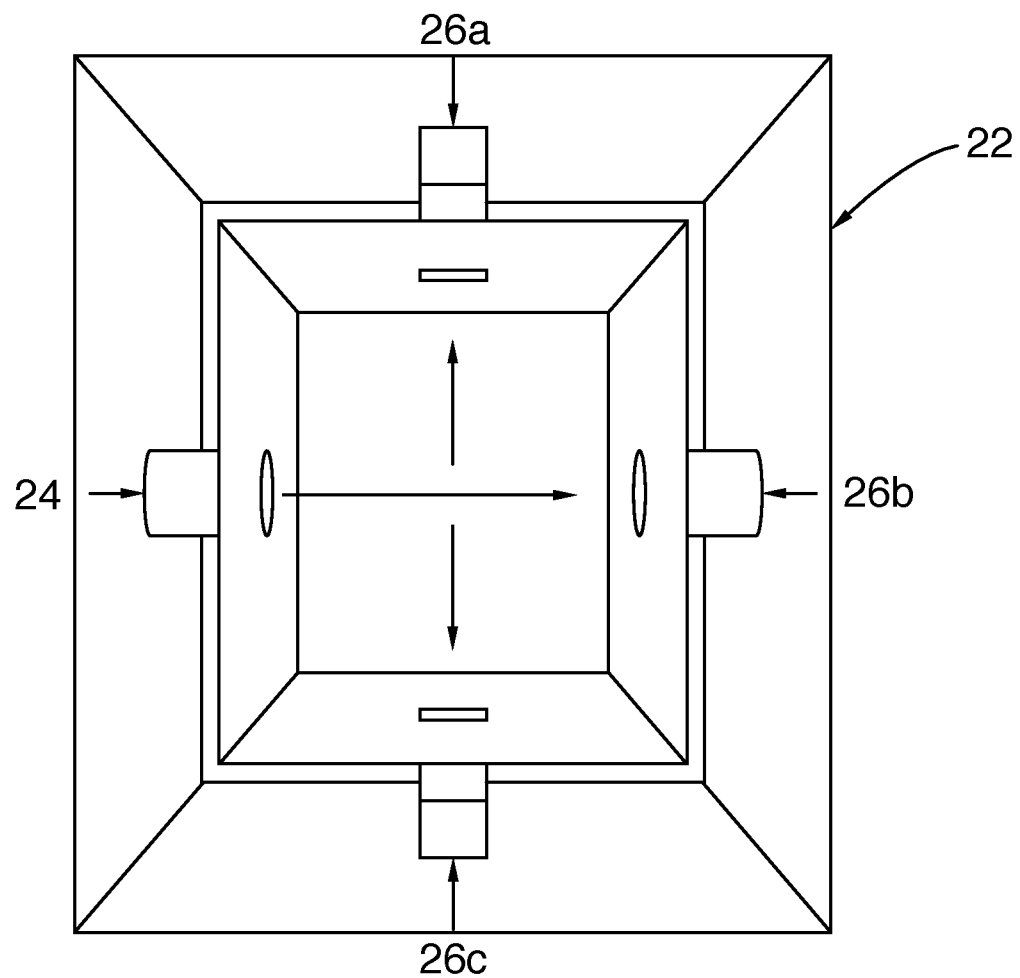
FIG. 1 shows a schematic drawing of the water flow and quality monitoring and control system in accordance with an embodiment of the present invention.
Figure 2:
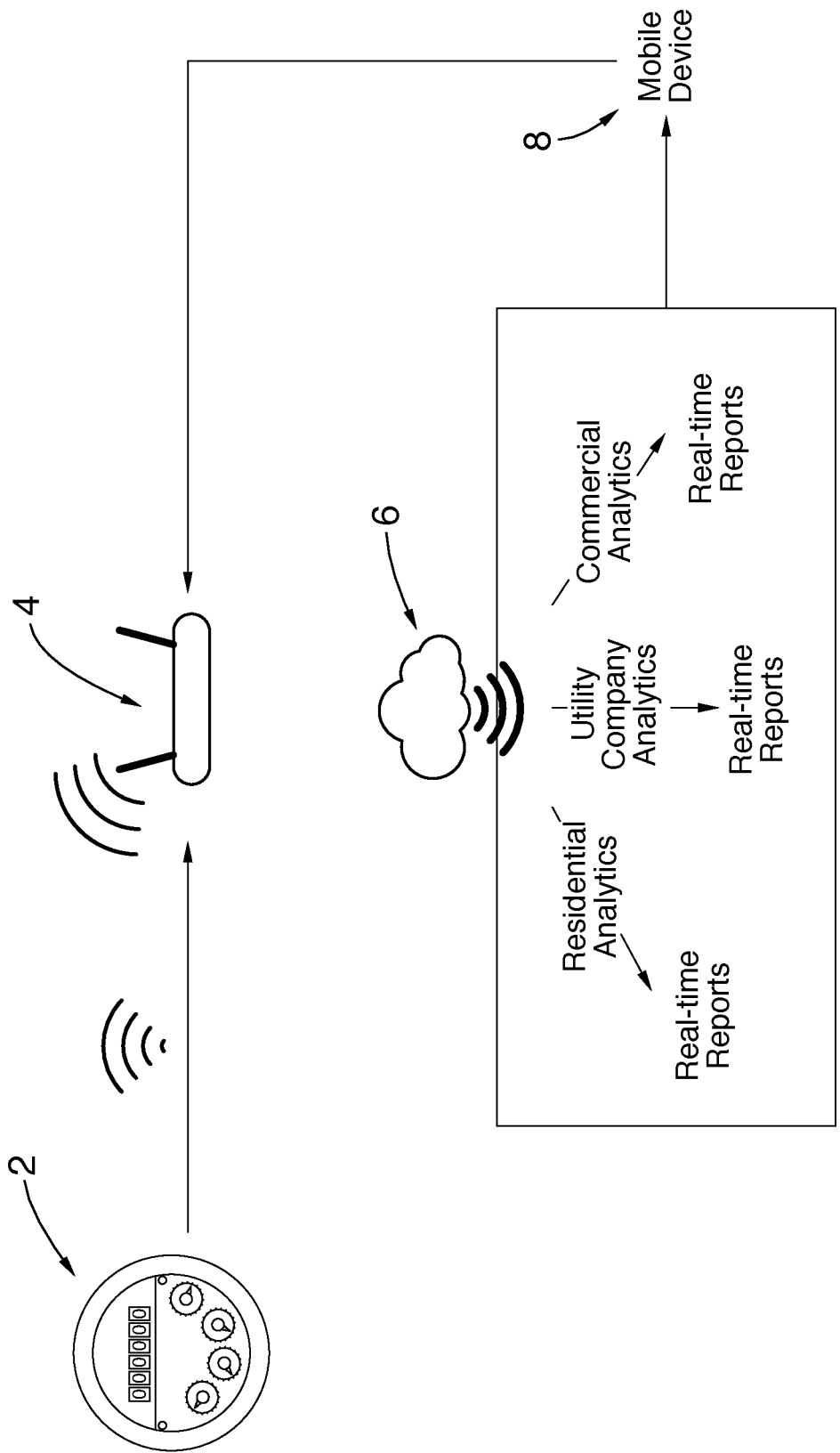
FIG. 2 shows a water meter/control and testing unit in accordance with an embodiment of the present invention.

FIG. 1 shows a schematic drawing of one of the embodiments of the water quality and quantity (e.g. flow) monitoring and control system, apparatus and methods. In a preferred embodiment, there is provided a turbidity sensor device ("TSD") 22 as may be shown in FIG. 1. In a preferred embodiment, TSD 22 detects turbidity in water samples by measuring how much light from a light source 24, such as, for example, a light emitting diode (LED) may be scattered or attenuated, such as, for example, by suspended particulates in the water flowing through the device or apparatus. In one embodiment, TSD 22 contains high power 850 nm LED light emitting source and three light transmission light to frequency converter detectors 26A, 26B, and 26C. Two of the light transmission detectors 26A and 26C detect scattered light and are oriented at, in a preferred embodiment, at approximately 90 degrees relative to a light source (e.g. LED 24). In a preferred embodiment, detectors 26A and 26C convert the scattered light signal into electrical pulses. In a preferred embodiment, the detectors 26A and 26C may be light to frequency detectors. The period between the pulses may be indicative of the amount of particulate within the sample (e.g. water flowing through the apparatus). In a preferred embodiment, a third detector (e.g. light to frequency detector) 26B may be oriented directly in line with the light source. The amount of light that reaches the detector 26B will be reduced based on the amount of particulate in the water flowing through the device. The amount of light detected by 26B may be converted into an electrical signal which may be correlated to the amount of particulate. All three sensors 26A, 26B, and 26C give a reading on the turbidity of the water. In a preferred embodiment, TSD 22 may be submerged in the water stream or flow through the apparatus or device and, in a further preferred embodiment, give readings of turbidity 40 (shown in FIGS. 4 and 5). In a preferred embodiment, the preferred range of would be 0 to 2.5 nephelometric turbidity units (NTU) or formazin turbidity units (FTU). The electrical signals are measured and processed with a small microcontroller (not shown) and turbidity data can be transmitted by the wireless processor (as shown in FIG. 2) or displayed on a computer screen (not shown) to the user. Most turbidity sensors are static instruments (e.g. LaMotte 2020we) and others are on-line (Thermo Scientific DataStick AquaClear).

A further preferred embodiment is provided in FIG. 2, wherein the system has a water quality and quantity monitoring apparatus that is connect to an external data receiving devices (e.g. the apparatus of the present invention is "networked"). The apparatus, systems and methods of the present invention identify the quantity and/or quantity of water as water flows through the device. In the case of measuring water quality, the amount of particles (e.g. suspended solids) in the liquid may be, in a preferred embodiment, determined in a dynamic state by measuring light scatter (see FIG. 1). In a preferred embodiment of the present invention as shown in FIG. 1, the turbidity sensor works at perpendicular (e.g. at approximately 90°) to the water flow by detecting scatter from pulsed light projected into the water flow (see above). In further preferred embodiments, additional sensors can be situated within the device body. In yet a further preferred embodiment, the sensors in the device housing may communicate with a circuit board having a microprocessor or microcontroller disposed therein for analysis of the sensor derived data or information and/or packages the data gathered from the sensors into data and/or information that can be analyzed within a database contained in a server. In a preferred embodiment, the board, processor etc. packages one or more data, information, signals, etc. (collectively data") gathered from the sensors and may then convert such data, information, signals, etc. into information that can be analyzed within a database provided within a server, which may be provided remote from the device. As used herein, it will be understood that the term "board" will refer to the circuit board having a microprocessor and/or microcontroller disposed therein. In a preferred embodiment, the board may contain known means for communicating, more preferably wirelessly, with a router 4 (shown in FIG. 2), in a manner that is well known to a person skilled in the relevant art. In a preferred embodiment, router 4 may receive sensor data, such as, for example, water characteristics, including but not limited to, water quality and water flow measurements (e.g. quantity) from water quality and monitoring device 2 of the present invention. In another preferred embodiment, the apparatus may also communicate the data to a cloud based server 6 (as shown in FIG. 2). Depending on the application and where the apparatus may be installed, the data can be shared, including with individual residential owners/users, utility companies, and/or commercial entities. From the data obtained from embodiments of the present invention, it will be understood that real time and/or non-real time reports can be generated, including, but not limited to details about specific water characteristics, including but not limited to, quality (e.g. ions, pathogens, etc.) and flow (e.g. quantity) and therefore alert users or others to current, historic or possible future conditions, such as any possible harmful effects of drinking and/or using the water. In a preferred embodiment, residential owners/user or consumers in general can use the data to set personalized water reduction goals, manage alert events for leaks, water characteristics, including but not limited to, quality, while providing the user, owner, consumer, etc. with educational information about how to reduce water use, better understand what may be in water and can have such functions as locations for advanced water quality testing. Commercial entities and utility providers can monitor or access water pressure, volume and quality of water entering a given building. Commercial entities and utilities data can be used to determine water pressure losses before or after entering a building, peak and low water use periods, leaks or turn off a service.

As shown in FIG. 2, the data obtained from the water quality and monitoring device 2 can then be provided, in a preferred embodiment, as a live feed or assembled into reports which can be accessed, for example using a mobile device 8 such as a tablet, mobile phone, etc. or a computer, such as a desk top or laptop (not shown). The user of the mobile device 8 or computer may then control aspects of the water quality and quantity monitoring apparatus 2, for example, such as, closing a control mechanism (e.g. a water shut off valve to prevent excess flow of water), receive real time alerts, etc. In a preferred embodiment, the control mechanism can be an electronic ball valve. In a further preferred embodiment, the control mechanism may also have a manual override.

Figure 3:
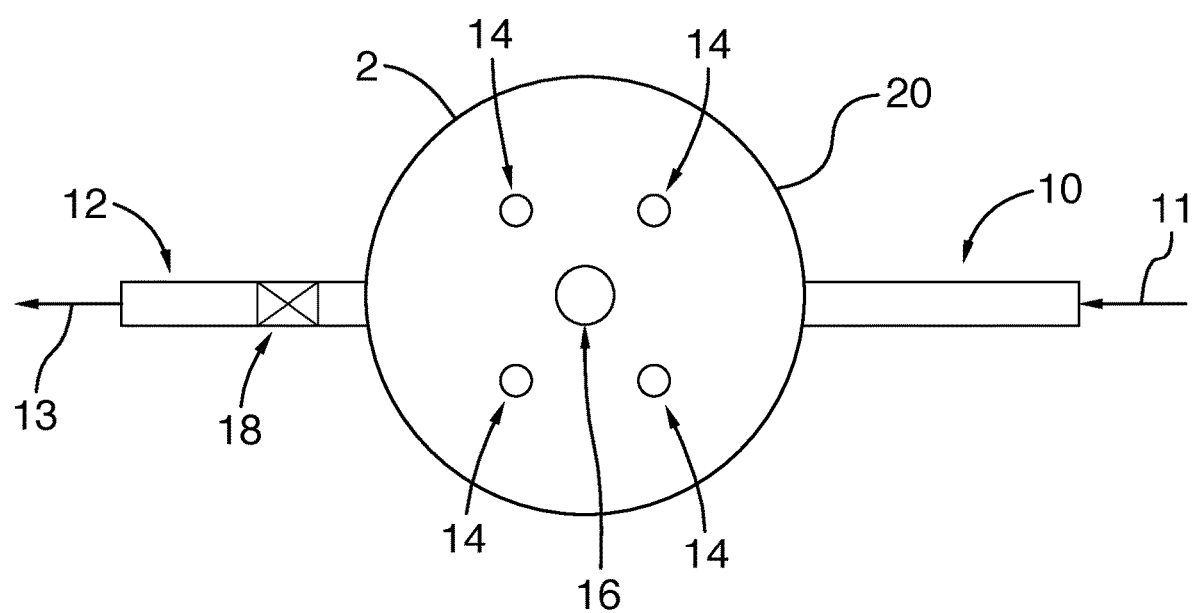
FIG. 3 shows a turbidity sensor in accordance with an embodiment of the present invention.

FIGS. 2 and 3 show preferred embodiments of the water monitoring apparatus of the present invention. It will be understood be a person skilled in the relevant art that components of the water quality and monitoring device 2 may be made of any suitable material, including, but not limited to PVC, ABS, brass, or any other suitable material known to a person skilled in the relevant art for the various fittings and components (lids, valves, sensor ports, etc.). The apparatus of the present invention can be designed to be connected directly to the plumbing of the desired location. This "in-pipe" configuration allows for increased functionality that may not be provided by other prior art systems. In-pipe sensing provides direct contact with passing or flowing water and an ability for directly detecting (and stopping) leaks as well as directly measuring water quality and quantity. It is preferred that water pressure measurements to determine leaks and multiple flow types (i.e. use of different water utilities in building—showers, sinks, toilets, washers) are superior to volume measurements. It is also preferred that water quality and quantity measurements be detected in the pipe as water quality cannot be detected without being in contact with a water stream. Although water flow can be detected without being in direct contact with water, pressure cannot be, which can be used to more accurately detect flow and especially leak events.

In FIG. 3, there is provided a schematic drawing of a preferred embodiment of the present invention. As shown in FIG. 3, the water quality and quantity device 2 has an inlet pipe 10 and outlet pipe 12 for water flowing into the device 2 from a location having a water supply source (e.g. city water main, pump, well, etc.). The water inlet flow is indicated by arrow 11; the water outlet flow is indicated by arrow 13. The water flowing into inlet pipe 10 flows through the device and comes in contact with the one or more water quantity and/or quality testing elements, apparatus, sensors or probes 14 (described in detail below). It will be understood that the sensors 14 will generally be referred to as "sensors". When an adverse event, fault or alert condition may be detected by a sensor 14, one or more control mechanisms (e.g. valves) can be manipulated accordingly (e.g. opened or closed). FIG. 3 provides for one control mechanism 18 along the water outlet pipe 12, but it will be understood that such control mechanisms can be provided on one or both of inlet pipe 12 or outlet pipe 10. In another embodiment, control mechanism 18 may be a manual, automated or otherwise electronic control valve which can be closed or shut manually, automatically or otherwise under electronic control, for example, in the event that a pipe has burst in a home and water flow exceeds a predetermined volume of water per unit of time, or a user may be notified via their mobile device of water flow and closes the valve provided in control mechanism 18. In another preferred embodiment, the water flow control mechanism 18 may be in communication with wireless processor 16 (see FIG. 3 and as described below) such that the valve can be opened and closed by wireless command, either initiated by a user or automatically. For example, if there may be excessive flow (as defined by average flow for building as determined by a system/data aggregation/analytics learning what flow is normally occurring) or pressure (>100 psi), loss of pressure of water detected, this may indicate the presence of a rupture in some portion of a water supply and usage system (not shown). The water supply and usage system refers to that portion of the normal plumbing system of a residence or a commercial building that receives water flowing through the outlet pipe 12. In a preferred embodiment, control mechanisms can be located before and after the sensing device or within the device itself.

In a preferred embodiment, specific methods may be used determine the nature of each water consuming or taking events (e.g. tap being turned on, dishwasher etc.), including adverse events or alert conditions, such as, for example, leaks. In the event of an adverse water event an alert may be sent to a location manager or owner who has the ability to take action either through direct onsite action or remotely (e.g. via a web dashboard). The water monitoring system of the present invention, employing apparatus 2, can detect whether the adverse event or alert condition (in the case of a leak, for example) may be internal to the user location (downstream from outlet pipe 13) or external to the user location (upstream from outlet pipe 10). In a preferred embodiment at least two control mechanisms 18 can be placed before and after the water quality and monitoring device 2 containing the sensors 14. Using a pressure sensor, the system can detect pressure prior or after the device using analytics in a corresponding server connected to the device. In a preferred embodiment, this can be done by the system performing verification tests. For example, if on control mechanism is shut off prior to the device/pressure sensor and pressure is observed to continue to decrease it can be determined that a leak is likely occurring after control mechanism. If, no pressure loss was observed then the leak may be occurring prior to the device/pressure and control mechanism.

Arrows 11 and 13 show the direction of flow of water through the device. The water quality and monitoring device 2 also has an outlet pipe 12 for water which has been analyzed and which flows out of the device 2 for use by a user. Within the water quality and monitoring device 2 are the testing apparatus, including probes/water quality testers. One or more of sensors 14 can detect and provide information about water quality and quantity, including, for example, the presence and/or concentration of elements in the water, such as (a) pathogens such as, for example, microorganisms, such as bacteria (including, but not limited to, *E. coli*, Heterotrophic Plate Count, total coliforms), enteric viruses and parasites (including, but not limited to *Legionella, Cryptosporidium, Giardia lamblia*); (b) mineral ion or other ion concentrations including, but not limited to, chlorine (chlorite, chloramines, chlorine dioxide), calcium, sodium. lead, copper, and heavy metals, including, but not limited to, arsenic species, and cadmium; (c) pH; (d) nitrogen (nitrate, nitrite, ammonia/ammonium); (e) temperature;

(f) turbidity from particulate matter in the water (e.g. organisms, solid matter, etc.); (g) water flow (e.g. volume per unit time) and (h) water pressure. In a preferred embodiment, each of the above noted parameters may have their own separate sensor; alternatively, sensors for the above noted parameters may be incorporated into a single sensor within the device 2. In a preferred embodiment, the water quality and monitoring device 2 has a wireless communication processor 16 (e.g. 802.11 b/g/n Radio Wi-Fi Driver or ZigBee IEEE 802.15.4 or Bluetooth protocols or Zwave)) that relays the water related data (e.g. quality and quantity) from the sensors 14 to the router or base station which then communicates with a wireless router 4. The wireless system would be run by a microcontroller with a Wi-Fi radio which allows for wireless communication to a Wi-Fi network or a router. In a more preferred embodiment, the device of the present invention would also support WPA2 personal and enterprise security systems and WPS 2.0. A Wi-Fi Internet-on-a-chip would include embedded TCP/IP and TLS/SSL stacks, HTTP server, and multiple Internet protocols.

Electrical power may be supplied to the apparatus 2. In a preferred embodiment, a power source (120V AC input and output 12V DC) 20 provides power to the apparatus 2. Battery backup (eg. 1050 mAh 3.7VC) (not shown) can also be provided in case of a power outage from an electrical utility provider so that the apparatus, system and methods of the present invention can still be operated during a power failure.

Figure 5:
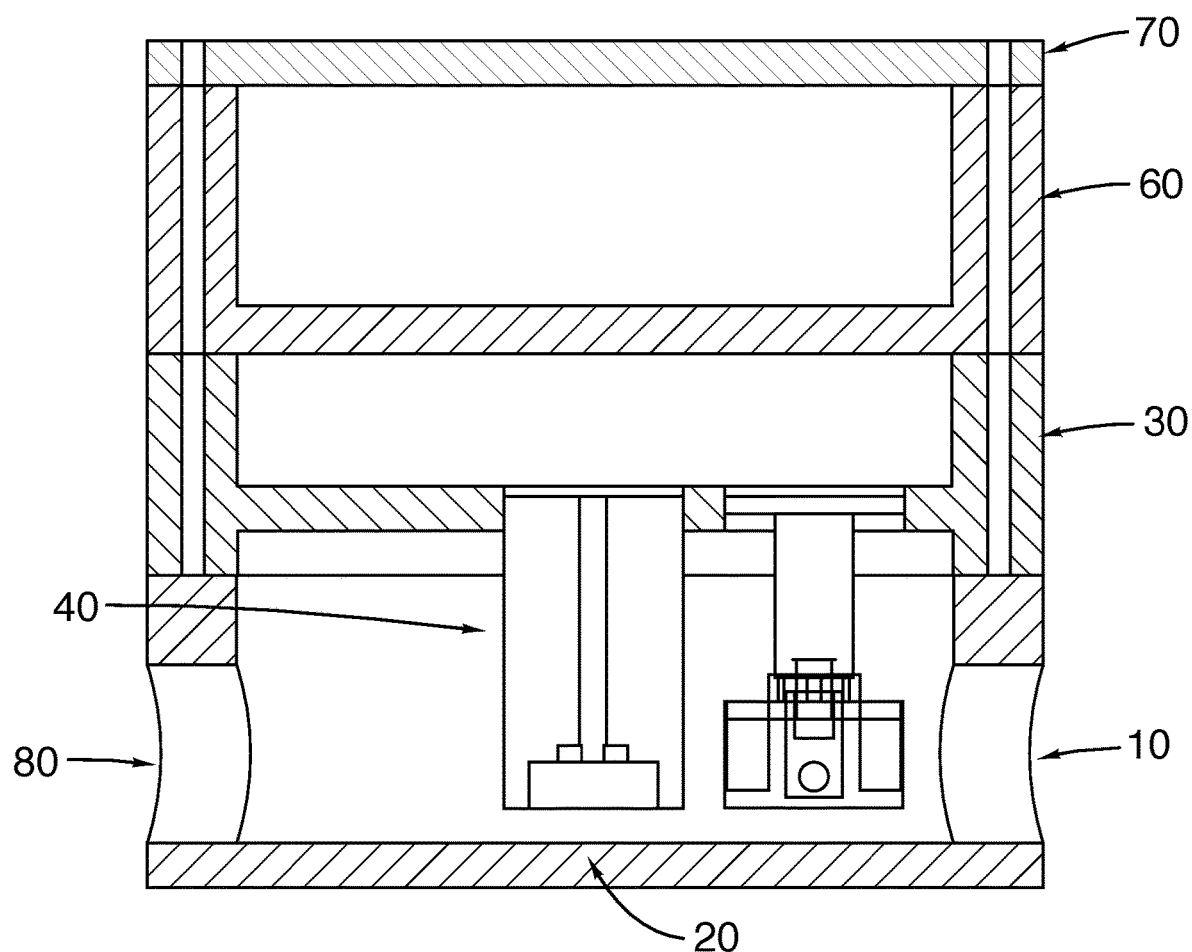
FIG. 5 shows a cross section view of the embodiment of FIG. 4 when assembled.
Figure 6A:
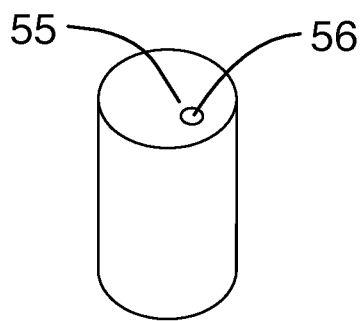
FIG. 6A to 6E shows further embodiments of the present invention.
Figure 6B:
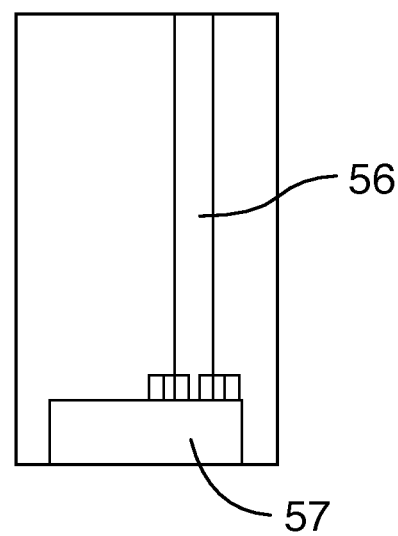
Figure 6C:
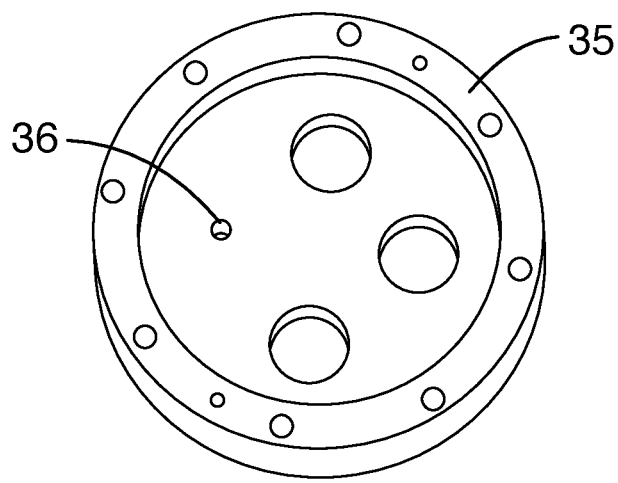

It may be appreciated that the water quality and monitoring device 2 can be constructed to be easily accessible in order to maintain/repair components, such as, for example, sensors 14, and also that the water quality and monitoring device 2 may be water tight. In other embodiments, the sensors 14 may be individually accessible from access ports in the housing of the water quality and monitoring device 2 (see FIGS. 4 to 6) so that sensors 14 can be individually repaired or replaced. Sensors are installed with sealed threading ports (see for example ports 35 in FIG. 6C). It may be further appreciated that the sensors 14 could be housed in separate apparatus, and not together in the same apparatus 2.

Figure 4:
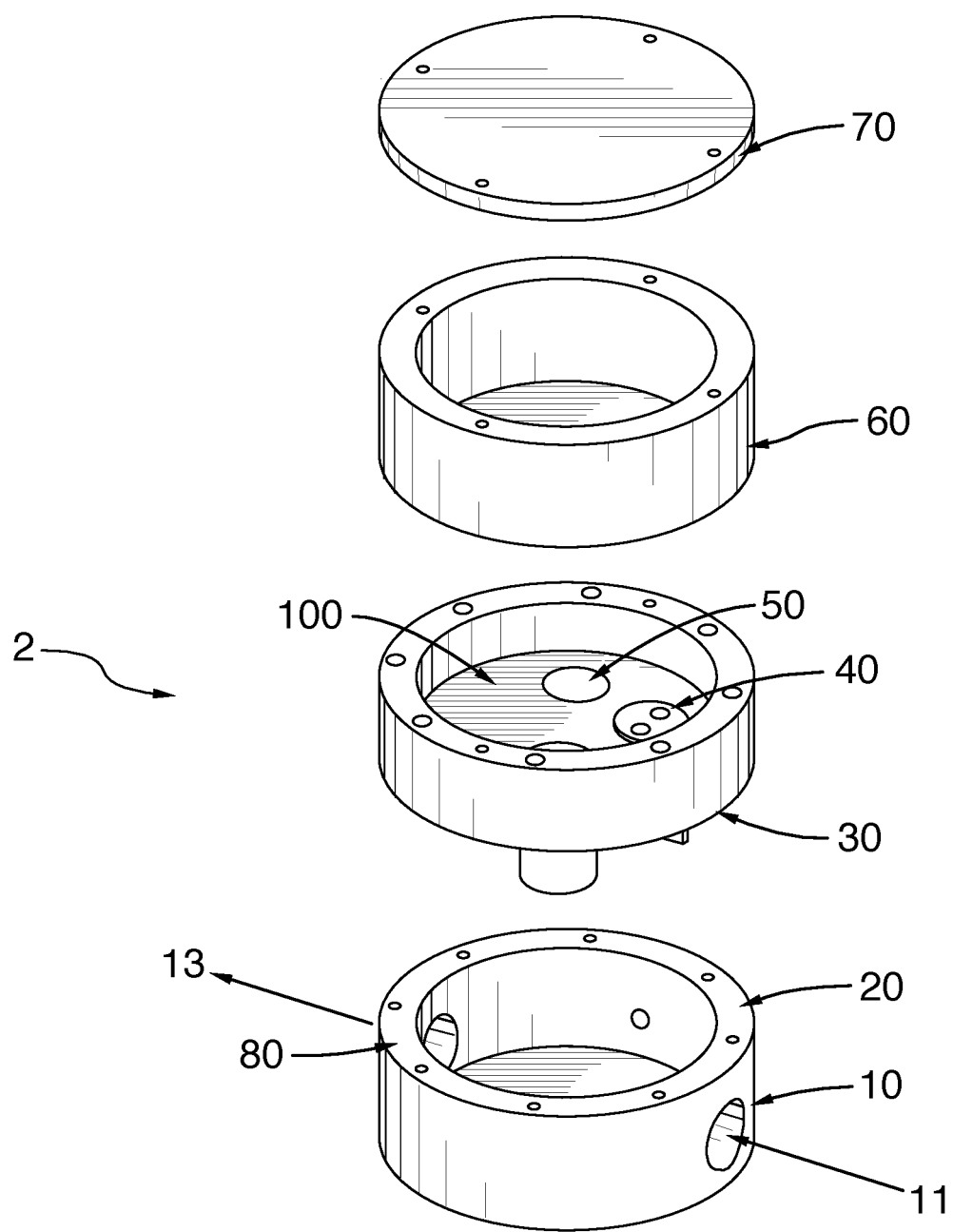
FIG. 4 shows an exploded perspective view of an embodiment of the present invention.

In a preferred embodiment of the present invention, the sensor zone (see FIG. 4, provided in sensor housing 30) and microcontroller zone (see FIG. 4, made in electronic housing 60) are separated by a waterproofed material (not shown). The housing body 10 may be designed to be damper proofed to prevent singular system breaches.

A preferred embodiment of the present invention is provided in FIGS. 4 to 7. As shown in FIG. 4, there is provided water quality and monitoring device 2 having a water flow housing 20 with an inlet flow opening 11 and an outlet opening 80. These can be attached to inlet pipe 10 and outlet pipe 12 respectively. There is also provided sensor housing 30 in which are disposed the sensors 14 (such as sensors 50) upon assembly. The electronic housing 60 is provided in which is disposed the microcontroller and/or microprocessor functionally connected (e.g. through wire channel 55 in FIG. 6A) to the sensors for analysing sensor data. Wire channel 55 provides a housing for the sensors to extend into the water flow (see FIG. 5). Once assembled, water related sensor data detected by a plurality of sensors disposed in the water flow (arrow 11 to arrow 13) provides water quality and quantity measures to the microcontroller and/or microprocessor. As shown in FIGS. 6A and 6B, wire channel 55 provides a tube 56 for allowing wires from the sensor disposed in recess 57 to connect to and transmitted the data to the microprocessor or microcontroller. It will be understood, however, that such data may also be transmitted wirelessly. Wire channel 55 may then be disposed with ports 35 of sensor housing 30. It will be understood by a person skilled in the relevant art that any arrangement of sensors 14 in the ports 35 is permitted.

The individual sensors of the present invention are described in greater detail below.

Temperature Detector

The temperature of the water may be determined by a thermocouple probe or sensor 100 disposed in thermocouple port 36. Preferred examples of thermocouple sensors of the present invention, include many well known in the art, including, for example, K-Type models. In a preferred embodiment, the electrical resistance at the thermocouple junction may be indicative of the temperature of the water. The electrical signal may be measured and processed by a microcontroller and temperature data can be transmitted by the wireless processor 16 for communication or displayed on a computer screen or mobile device as noted above.

Chlorine Detector and Other Ions

The concentration of mineral ions or other ions (calcium, sodium, etc.) in water streams may be detected by sensors which may be provided in sensor receiving recess 57 that may be submerged into the water stream. Preferred embodiments include, such as, for example, Kapta 3000-AC4. In a preferred embodiment, such a sensor may be a membrane covered electrode to allow for selective ions to pass to the electrodes or bare electrode to measure total free ion chlorine. The electrodes detect and measure electrical signal (e.g. of system through ion exchange) which may be processed by microcontroller (as described above) and mineral or other ion data can be transmitted by the wireless processor 16 for communication or displayed on a computer screen or mobile device. In a preferred embodiment, the system and/or method of the preferred embodiment can incorporate regulated limits set by applicable authorities (e.g. city, municipality, state, province, etc.) for the presence (and/or absence) of mineral or other ion values or concentrations in the analyzed water. Other ions could be integrated, such as a fluoride sensor, and an iron sensor or other ions and/or minerals that can be detected through ion exchange or optical means.

Nitrate Detector and Other Ions

In a preferred embodiment, the nitrate in the water stream may be detected by a probe which may be one of the sensors 14 that may be submerged into the water stream (e.g. in a preferred embodiment, ABB AV450, UV Nitrate Monitor, etc.). In a preferred embodiment, the nitrate probe can be made up of an electrode that has a membrane or lacks a membrane (solid state) for ion selectivity. The microprocessor or microprocessor can receive a signal from select ions, and determine the concentration of thereof in the water stream. The nitrate data can then be transmitted by the wireless processor 16 for communication or displayed on a computer screen or mobile device (not shown) (see FIG. 2). As noted above with regard to chlorine and/or other mineral ions, the system and method of the present invention can determine the presence or absence of nitrate values above or below regulated limits. Other ion sensors could be included, such as ammonia and phosphates.

pH Detector

The pH in the water stream may be detected by a sensor which may be one of the sensors 14 that may be submerged into the water stream. Preferred embodiments of such detector include, but are not limited, Hach pHD sc and Online Process pH Sensor. In a preferred embodiment, the probes of the present invention can be solid state or membrane based to allow for detection of H+ or OH− ions. Ions can either pass through the sensor or pass by through a detection. In a further preferred embodiment, the pH probe can send a signal to the wireless processor 16 communication or displayed on a computer screen or mobile device. The processor determines the pH value. The system can acknowledge the presence or absence of pH values above or below regulated limits.

Pathogen Detector

Figure 6D:
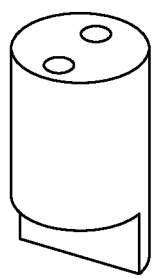
Figure 6E:
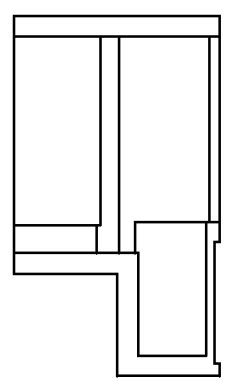
Figure 7A:
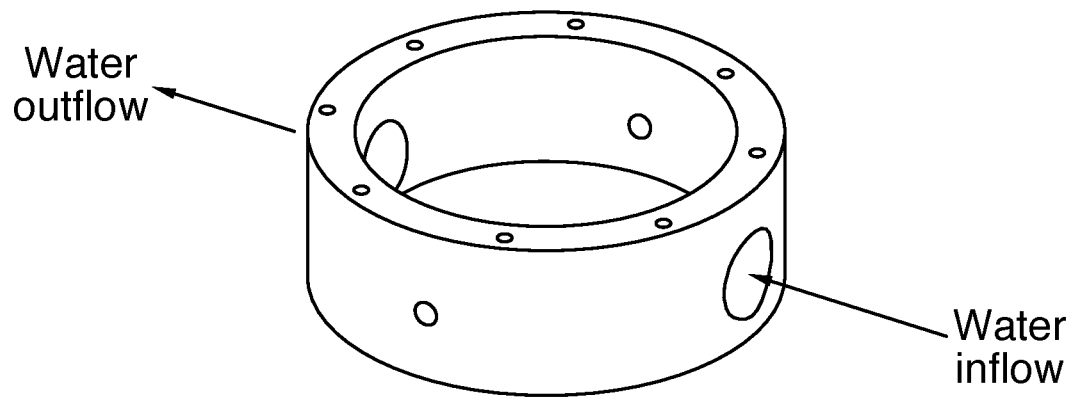
FIGS. 7A and 7B show further embodiments of the present invention.
Figure 7B:
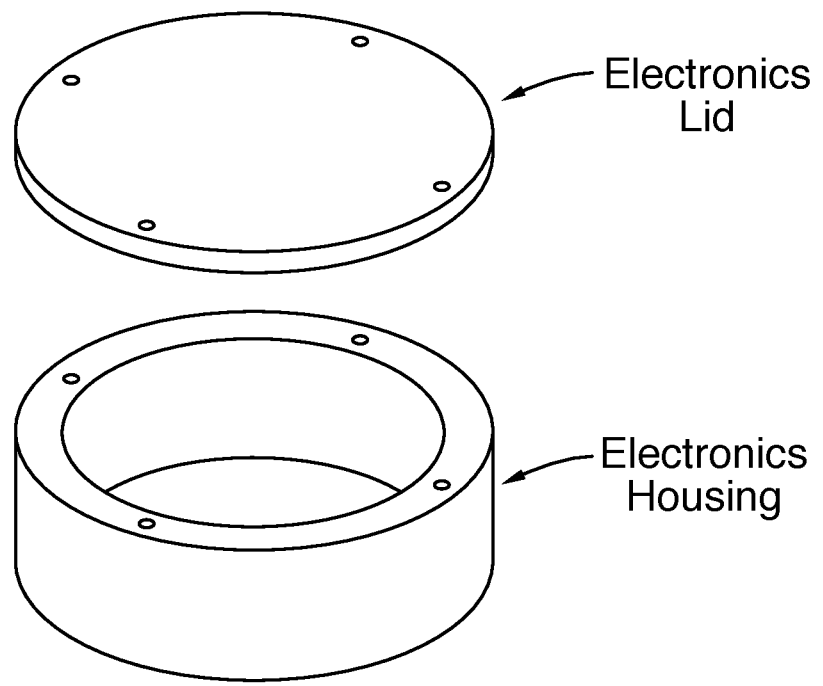

A detector to measure and/or detect pathogens such as microorganisms, including bacteria (e.g. *E. coli*, coliforms, etc.) can be placed in stream or take water from the stream. As shown in FIGS. 6D and 6E, there is provided turbidity sensors provided in housing 60. The device can measure colony forming units or can measure a representative form of the presence of bacteria from, for example, increased turbidity. This sensor can indicate possible contamination via bacteria colonies that have greater potential to be present in water with higher levels of turbidity, or indicate other potential contaminants ranging from lead to various ions (e.g. nitrate). In a preferred embodiment, microorganism related data can be transmitted by the wireless processor (as described above for other sensors) 16 for communication or displayed on a computer screen or mobile device (not shown). In yet a further preferred embodiment, the system or method of the present invention can incorporate and/or acknowledge the presence or absence of bacteria values above or below regulated limits.

Pressure Sensor

In a preferred embodiment, the "in-pipe" (e.g. internal) pipe pressure may be determined by a small electrical sensor (e.g. 0-400 bar ceramic piezoresistive sensor 90 (shown in FIG. 4)). In a preferred embodiment, the pressure may be converted into an electrical signal and may be measured and processed by a microcontroller (as described above). In a preferred embodiment, pressure data can be transmitted by the wireless processor 16 for communication or displayed on a computer screen (not shown). The pressure can be used to detect leaks, provide information on flows of different appliances in buildings. There are numerous pressure sensors products which can be used in the present invention. In yet another preferred embodiment, piezoresistive pressure sensors with a range 0 to 100 bar, with a temperature range of −20-80 C are included. Yet another preferred embodiment includes, but is not limited to, Series M5 Pressure Transmitter.

Volume of Flow

The volume of flow of water may be determined by a pressure sensor and flow sensor which may be one of the sensors 14. A preferred embodiment is a DC 5V~24V electrical turbine or ultrasonic flow meter. The flow rate may be related to the change in pressure and may be measured over time. When a pressure change occurs, a microcontroller within a preferred embodiment of the device of the present invention, calculates the flow rate. Flow rate is derived from pressure change—a static pressure reading is an indication of zero flow and decreasing pressure reading is indicative of velocity. The amount of time the microcontroller reads the pressure change may be calculated and may be multiplied by the instantaneous flow rate to gives an instantaneous volume. The instantaneous volume can be tallied to give the total volume accumulation. Similar with the flow sensor, the rotations of turbine can be used to determine flow in the case—the volume calculation in this device can use one or both of the methods. These signals are measured and calculated with a small microcontroller and the results can be transmitted by the wireless processor 16 for communication or displayed on a computer screen (not shown).

Although this disclosure has described and illustrated certain preferred embodiments of the invention, it may be also to be understood that the invention may be not restricted to these particular embodiments rather, the invention includes all embodiments which are functional, or mechanical equivalents of the specific embodiments and features that have been described and illustrated herein. It will be understood that, although various features of the invention have been described with respect to one or another of the embodiments of the invention, the various features and embodiments of the invention may be combined or used in conjunction with other features and embodiments of the invention as described and illustrated herein.

The embodiments of the invention in which an exclusive property or privilege may be claimed may be defined as follows:

The invention claimed is:

1. A method for detecting whether the cause of a reduction in water pressure flowing through a pipe into a user location is internal to the user location or external to the user location, the method comprising:
   (a) installing an in-pipe water pressure monitor at a location proximate to the water inlet of the user location, the monitor including a water flow through the monitor during operation, a first controller located in the pipe and a second controller located in the pipe, the first controller located upstream from the monitor but downstream of the water inlet of the user location, and the second controller located downstream from the in-pipe water pressure monitor but upstream of the water outlet of the user location;
   (b) detecting the water pressure loss within the monitor; and
   (c) shutting off the first controller and determining if there is a pressure loss detected within the monitor;
   (d) wherein if a pressure loss is detected, the cause of the reduction in water pressure is internal to a user location and if a pressure loss is not detected the cause of the reduction in water pressure is external to the user location.

2. The method of claim 1, wherein the user location is a residence or commercial building.

3. The method of claim 2, wherein at least one of the controllers is a water valve.

4. The method of claim 3, wherein at least one of the first controller and the second controller, allows a user to shut off the flow of water manually or automatically upon detection of the pressure loss.

5. The method of claim 4, wherein the in-pipe water pressure monitor further comprises:
   a housing having a water inlet port disposed in the pipe and a water outlet port disposed in the water flow;
   a processor disposed with the housing; and
   a water quality measurer in the housing and disposed in the water flow operably measuring water pressure within the water flow and transmitting the water pressure loss to the processor.

6. The method of claim 5, wherein the processor wirelessly transmits the water pressure loss to a remote server.

7. The method of claim 6, wherein the water pressure loss is provided to at least one of: residential users, utility companies, and commercial entities.

* * * * *